United States Patent [19]
Taylor et al.

[11] Patent Number: 6,045,567
[45] Date of Patent: Apr. 4, 2000

[54] LANCING DEVICE CAUSING REDUCED PAIN

[75] Inventors: William C. Taylor, Rex; Richard Wayne LeVaughn, McDonough, both of Ga.; John M. Purlee, San Jose, Calif.; Christopher John Ruf, Atlanta, Ga.

[73] Assignee: Lifescan Inc., Milpitas, Calif.

[21] Appl. No.: 09/255,918

[22] Filed: Feb. 23, 1999

[51] Int. Cl.[7] ................................................. A61B 17/14
[52] U.S. Cl. ........................... 606/181; 606/182; 600/573
[58] Field of Search .................................. 606/181, 182, 606/183, 184, 185; 600/573, 538, 578, 576, 574, 575

[56] References Cited

U.S. PATENT DOCUMENTS

| | | | |
|---|---|---|---|
| 4,503,856 | 3/1985 | Cornell et al. ........................... | 128/314 |
| 4,527,561 | 7/1985 | Burns ....................................... | 128/314 |
| 4,535,769 | 8/1985 | Burns ....................................... | 128/314 |
| 4,553,541 | 11/1985 | Burns ....................................... | 128/314 |
| 4,895,147 | 1/1990 | Bodicky et al. ......................... | 606/182 |
| 4,976,724 | 12/1990 | Neito et al. .............................. | 606/182 |
| 5,318,584 | 6/1994 | Lange et al. ............................. | 606/182 |

*Primary Examiner*—Michael Buiz
*Assistant Examiner*—Lien Ngo
*Attorney, Agent, or Firm*—James Riesenfeld

[57] ABSTRACT

A lancing device has a spring-loaded lancet holder slidably mounted within a housing for carrying a disposable lancet and needle. A knob on the back of the device has forward-extending fingers that stop the lancet holder at an adjustable predetermined point after the device has been fired. The fingers not only control the penetration depth of the needle, but also absorb vibrations and reduce noise to cause less pain to the user.

3 Claims, 7 Drawing Sheets

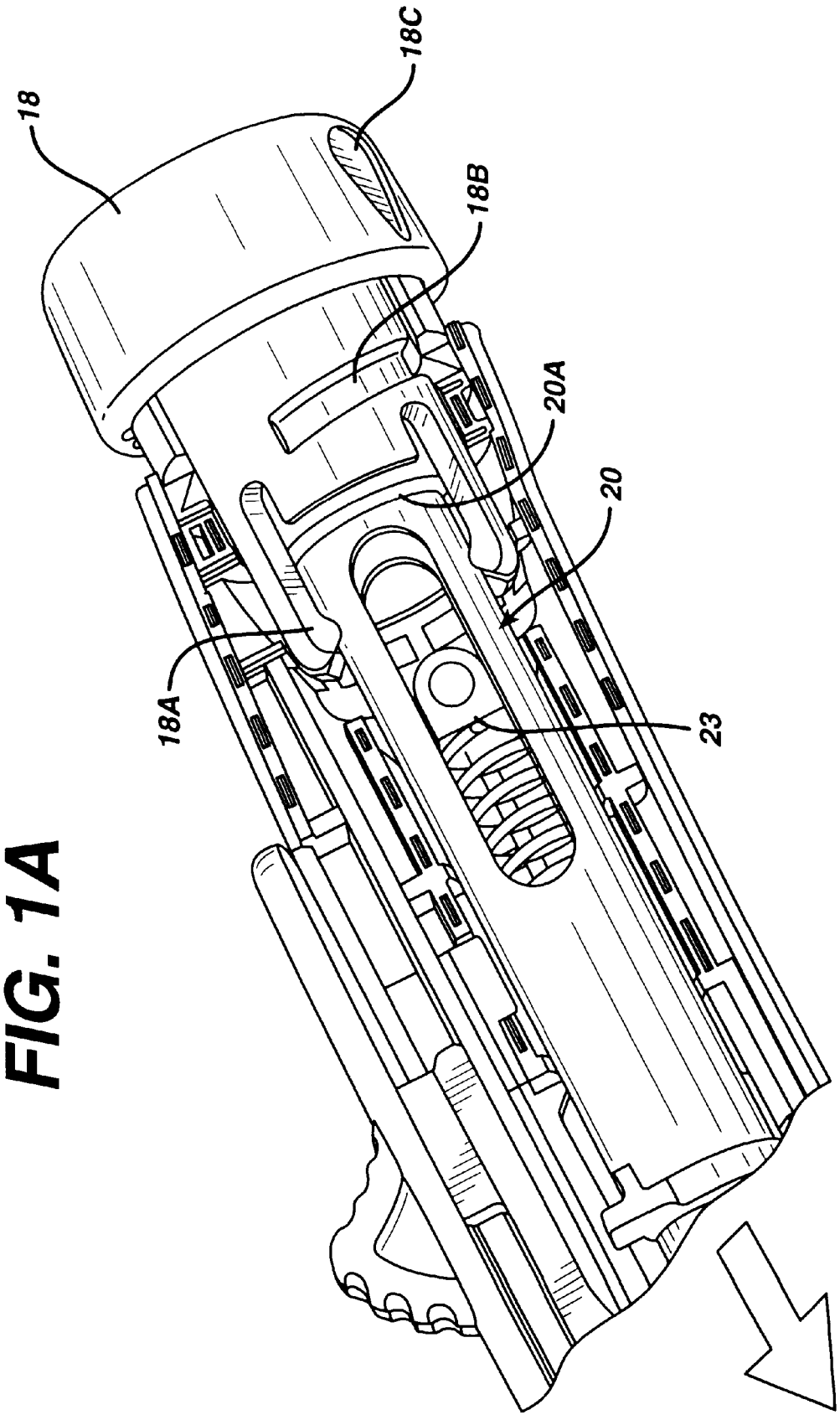

LANCING DEVICE CAUSING REDUCED PAIN

BACKGROUND OF THE INVENTION

1. Field of the Invention

This invention relates to a lancing device to pierce the skin to obtain a blood sample; more particularly, a lancing device that causes less pain for the user.

2. Background of the Related Art

Lancing devices are an unfortunate fact of life for the millions of people with diabetes who must test their blood glucose levels up to five or more times each day. They typically use the devices to draw a drop of blood from a finger, apply the blood to a disposable strip, and measure the blood glucose concentration in a meter. Obvious goals of such lancing devices are to provide an adequate sample of blood with minimal pain, inconvenience, and cost to the user.

U.S. Pat. No. 4,503,856, issued on Mar. 12, 1985 to Cornell et al., discloses a lancet device that has a tubular housing, a slidable lancet holder in the housing and a compressible spring that provides the force to move the holder linearly to a skin piercing position, after which it goes back to a neutral position.

U.S. Pat. No. 4,527,561, issued on Jul. 9, 1985 to Burns, discloses a lancet assembly that includes a second spring for retracting the lancet holder after the lancet has penetrated the user's skin (see also U.S. Pat. Nos. 4,535,769 and 4,553,541).

U.S. Pat. No. 4,895,147, issued on Jan. 23, 1990 to Bodicky et al., discloses a lancet device that includes a penetration depth selector and a mechanism for creating a vacuum after the skin has been pierced to assist in drawing blood from the puncture site.

U.S. Pat. No. 4,976,724, issued on Dec. 11, 1990 to Nieto et al., discloses a lancet device that includes a mechanism that permits the user to eject a used lancet without touching it.

U.S. Pat. No. 5,318,584, issued on Jun. 7, 1994 to Lange et al., discloses a lancet device that includes a rotary/sliding transmission system that permits a puncture to be made with adjustable/reproducible penetration depth and with less pain.

SUMMARY OF THE INVENTION

The present invention provides a lancing device for withdrawing a blood sample. It comprises a generally elongate housing having a cap with a through hole at a forward end and containing (a) a lancet holder, slidably mounted within the housing,
(b) a first spring for urging the holder forward, having a first end that bears on the housing and a second end that bears on the holder,
(c) a slider, slidably mounted in a wall of the housing, comprising
   (i) a projection outside the wall and
   (ii) a pushing means, reversibly engageable with the holder, to push the holder back into a cocked position and to push a lancet forward from the device,
(d) a second spring for urging the holder back, having a first end that bears on the holder and a second end that bears on the slider,
(e) a button, movable between a first position in which the holder is restrained when the device is cocked and a second position in which the restraint is removed, permitting the first spring to thrust the holder forward, and
(f) a closure at the back end, comprising
   (i) a plurality of forward-extending elements for stopping the forward motion of the holder at a predetermined position and
   (ii) adjustment means for controllably changing and resetting the predetermined position.

The present device causes less pain during the lancing procedure, because needle oscillations and noise are reduced as compared with lancing devices of the prior art. In addition, controlling penetration depth from the rear of the device provides advantages over devices in which depth control is at the front. It permits the present device to have an inexpensive front cap, which is desirable because contamination of the cap may require that it be replaced. In addition, by controlling penetration depth at the rear of the device, it is less likely that the depth setting will be obscured by the fingers holding the device.

BRIEF DESCRIPTION OF THE DRAWINGS

FIG. 1A is an enlarged view of the back end of the device of FIG. 1.

DETAILED DESCRIPTION OF THE INVENTION

Figure 1:
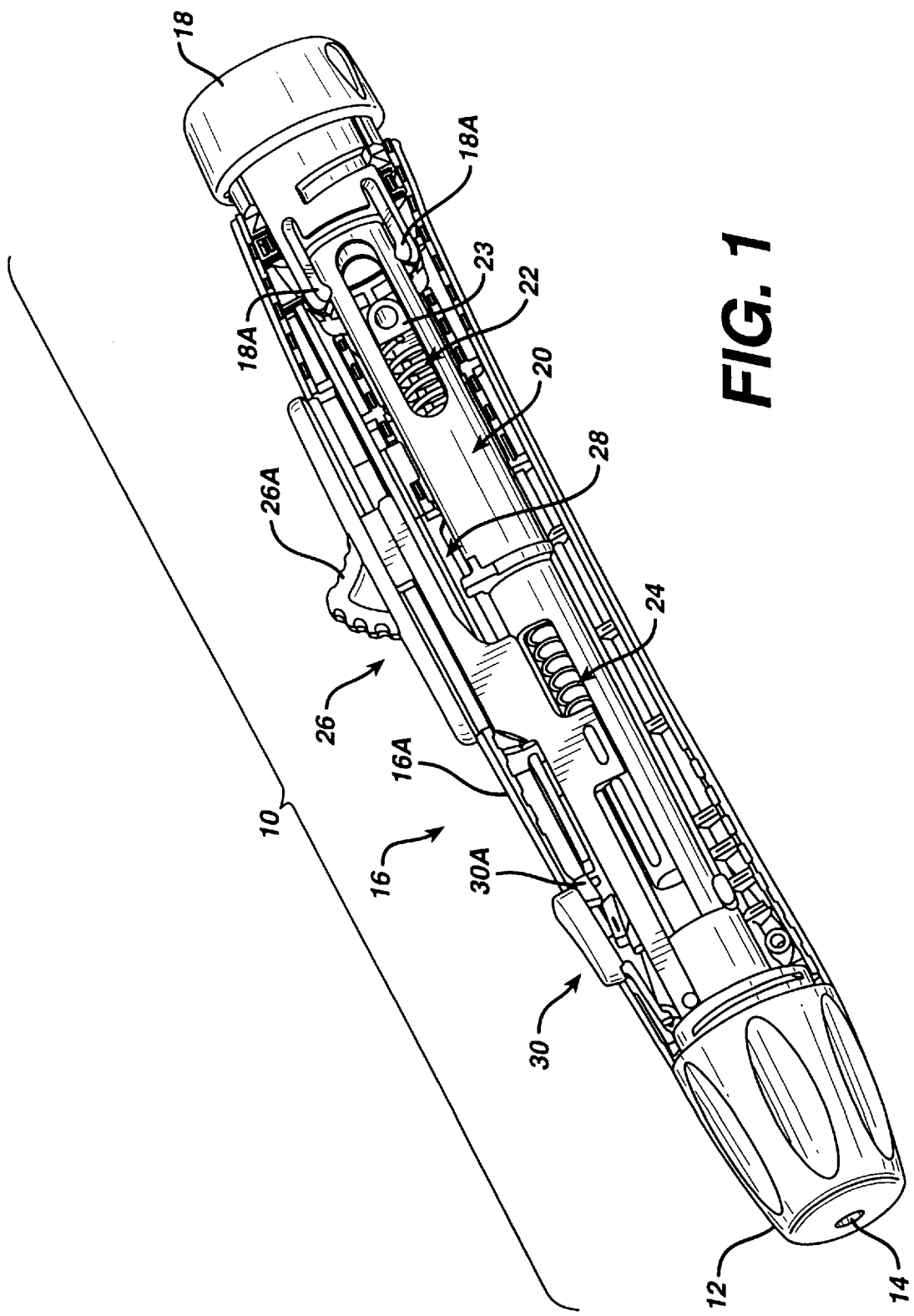
FIG. 1 is a perspective view of a device of this invention with half the housing removed.

The present invention provides a lancing device that provides a noise- and vibration-reducing mechanism for causing reduced pain during the lancing operation. FIG. 1 depicts a lancing device 10 of this invention, with one side of the housing removed to permit a view of the interior. The front end of the device has cap 12, with through hole 14. Cap 12 is removably joined, for example by a screw thread, to the housing 16, which is conveniently of two parts. One half 16A is shown, while the other half has been removed. At the back end of the device opposite cap 12, housing 16 is joined to knob 18. Knob 18 has cantilever fingers 18A that provide a mechanical stop, whose position can be varied by a thread, such as a helical thread, that attaches the knob to the housing.

A lancet holder 20 holds and guides a disposable lancet throughout the operation of the device. A drive spring 22 stores the energy needed for driving the lancet forward. Drive spring 22 is contained within holder 20 and bears on post 23 of the housing. A second, "retraction" spring 24, also contained in holder 20, provides a mechanism for removing the lancet needle from the skin after the skin has been punctured. The spring constant of retraction spring 24 is substantially less than that of drive spring 22; thus, drive spring 22 is substantially "stronger." Slider 26 is slidably mounted on housing 16 and has a projection 26A outside the housing that is manually movable—back to cock the device and forward to eject the lancet. When the device is being cocked, slider 26 engages holder 20. Button 30 is mounted through the housing, with tab 30A projecting inside the housing. After the device is cocked, pushing button 30 releases the restraint on lancet holder 20 to permit spring 22 to thrust the holder forward. Reference to element 30 as a "button" is not to suggest that the actuator element pictured is the only one contemplated. As used in this specification and the appended claims, "button" is to be understood as applying broadly to any actuator, of the type well known in the art, that can release the restraint on the lancet holder.

FIG. 1A depicts an enlargement of the rear part of the lancing device 10. In a preferred embodiment of the mechanical stop feature, depicted there, cantilever fingers 18A, which extend forward from knob 18, have undercut forward ends, which form inward-extending protrusions. When holder 20 moves forward, in the direction shown by the arrow on the left, holder ledge 20A ultimately contacts the protrusions on cantilever legs 18A. The force of the holder ledge 20 causes the fingers to flex, which dampens or absorbs the vibration of the impact and reduces the noise. Both these effects reduce the pain caused to the user. The position of the protuberances relative to the front of the device determines how deeply the lancet needle will penetrate the skin. That position, in turn can be adjusted by turning the knob 18, which rides on thread 18B. Indicator 18C on the knob, in combination with markings on the housing (not shown), permit the device to be set to given variable and reproducible puncture depths. Variable puncture depths are desirable, because the user generally wishes to provide just enough blood for the particular test and because the characteristics of the fingers of users are different. By providing a depth range of about 1.8 mm in 7 approximately equal steps, the needs of nearly all potential users can be met.

The operation of the lancing device can be understood with the help of a series of FIGS. that show the configuration of the elements of the device in sequence during device operation.

Figure 2:
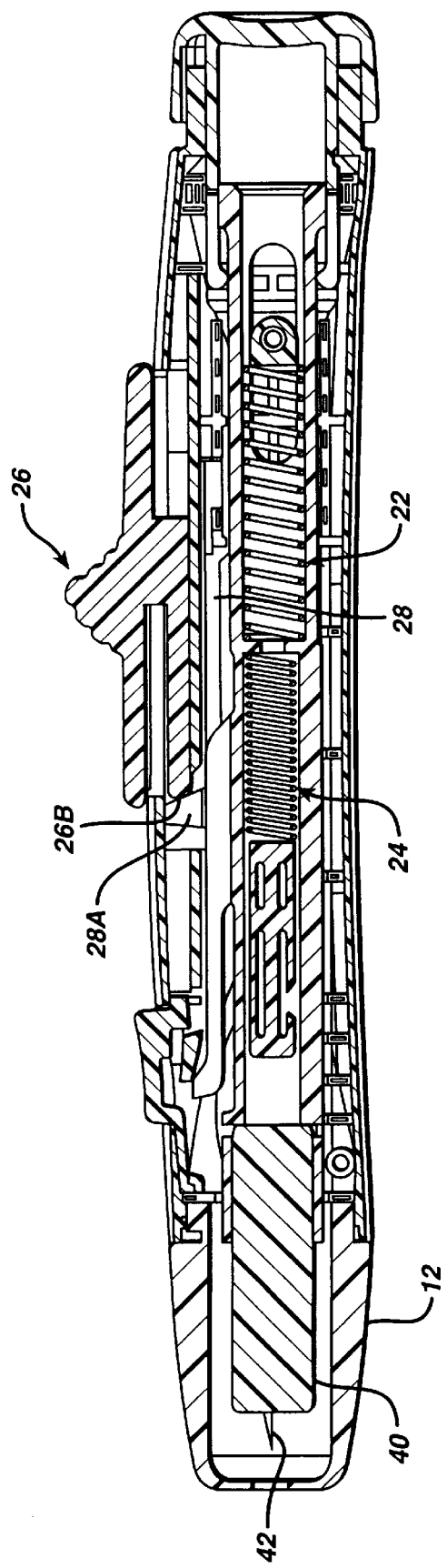
FIG. 2 is a cross section of the device of FIG. 1 in its rest position.

FIG. 2 shows a cross section of the device at rest, with the internal part 26B of slider 26 resting against top 28A of releasable connector 28. Drive spring 22 and retraction spring 24 are in balance, bearing on one another. Both springs are compressed, drive spring 22 much less than return spring 24, because its spring constant is much larger. Lancet 40 and needle 42 are seen inside cap 12.

Figure 3:
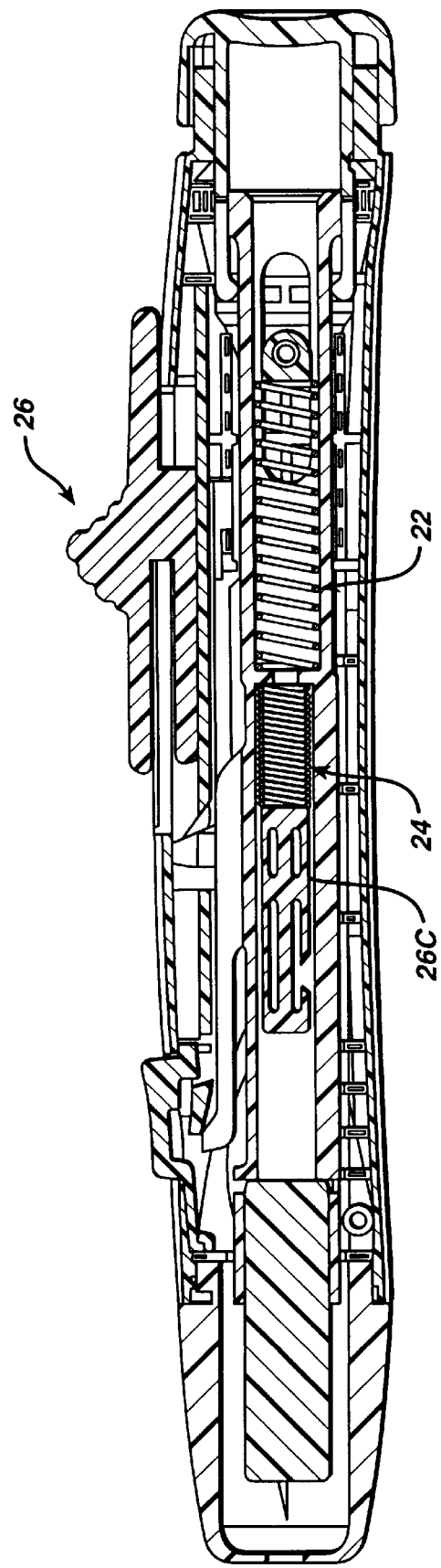
FIG. 3 is a cross section of the device of FIG. 1 as it is being cocked.

FIG. 3 shows a cross section of the device in an intermediate position as it is in the process of being cocked, by slider 26 being moved back (to the right in FIG. 3). The force exerted by the backward motion of pushing element 26C of slider 26 causes retraction spring 24 to be compressed more than in FIG. 2. Because of its much larger spring constant, drive spring 22 remains relatively uncompressed.

Figure 4:
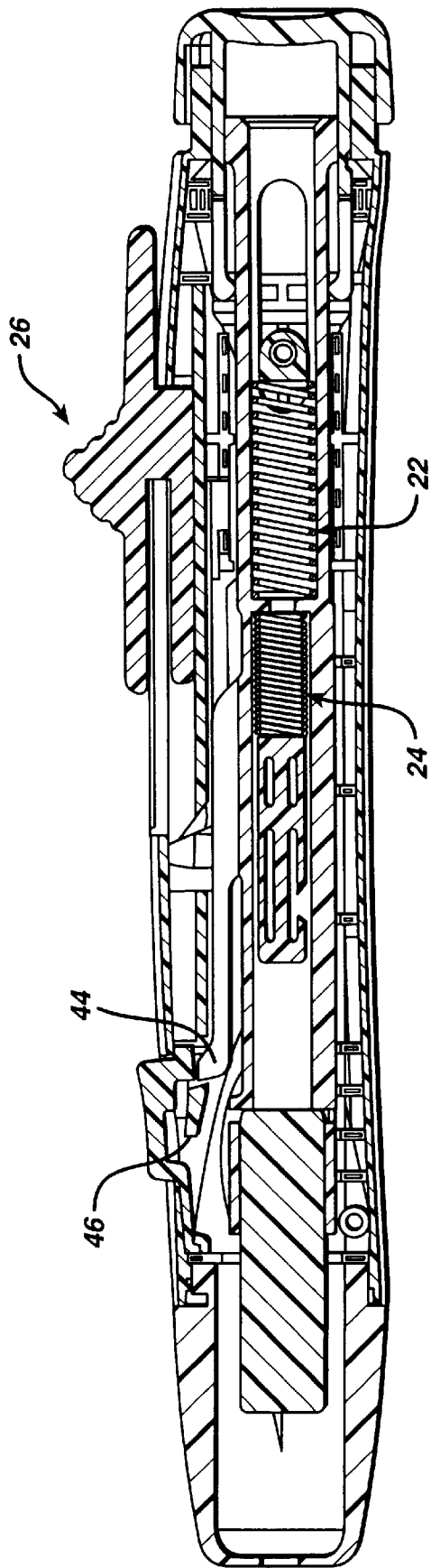
FIG. 4 is a cross section of the device of FIG. 1 in the over-cocked position.

FIG. 4 depicts the lancing device when it is in the "over-cocked" position; i.e., slider 26 has been moved to the far rearward position of its travel. Cantilever extension 44 of lancet holder 20 has moved slightly beyond (to the right of) housing stop 46. Drive spring 22 is compressed and retraction spring 24 remains compressed to about the same degree as in FIG. 3.

Figure 5:
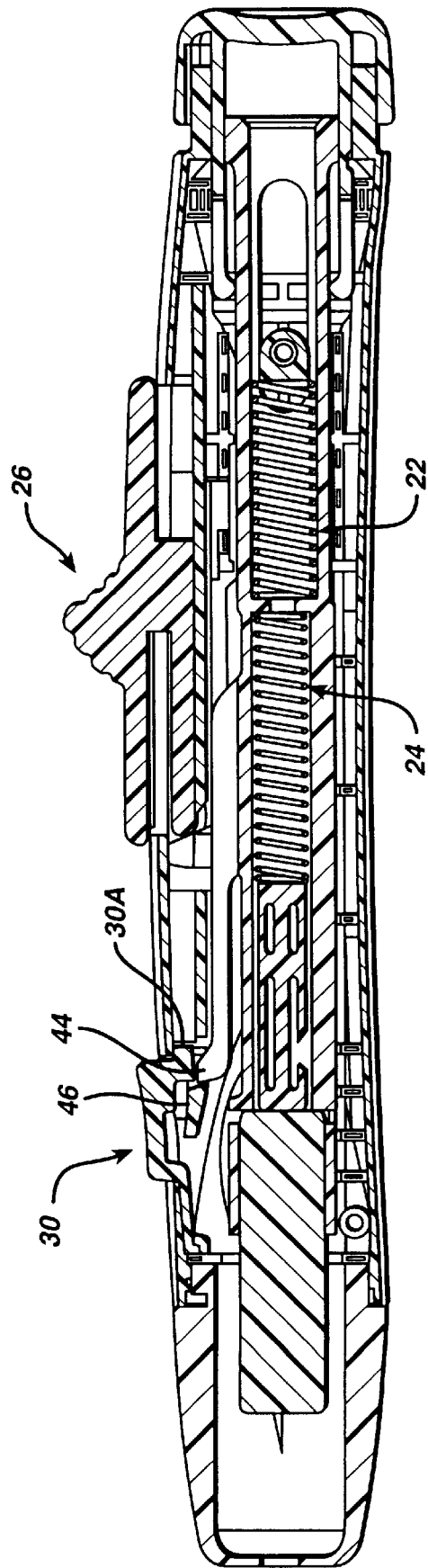
FIG. 5 is a cross section of the device of FIG. 1 when it is cocked.

FIG. 5 depicts the lancing device when it is cocked and at rest. Drive spring 22 is forcing extension 44 of lancet holder 20 against housing stop 46. Slider 26 has returned to its initial (FIG. 2) position. Retraction spring 24 is less compressed than in FIGS. 3 and 4. If button 30 is now pushed, tab 30A pushes extension 44 free of (under) stop 46 and enables lancet holder 20 to be thrust forward (to the left) in response to the force exerted by compressed drive spring 22.

Figure 6:
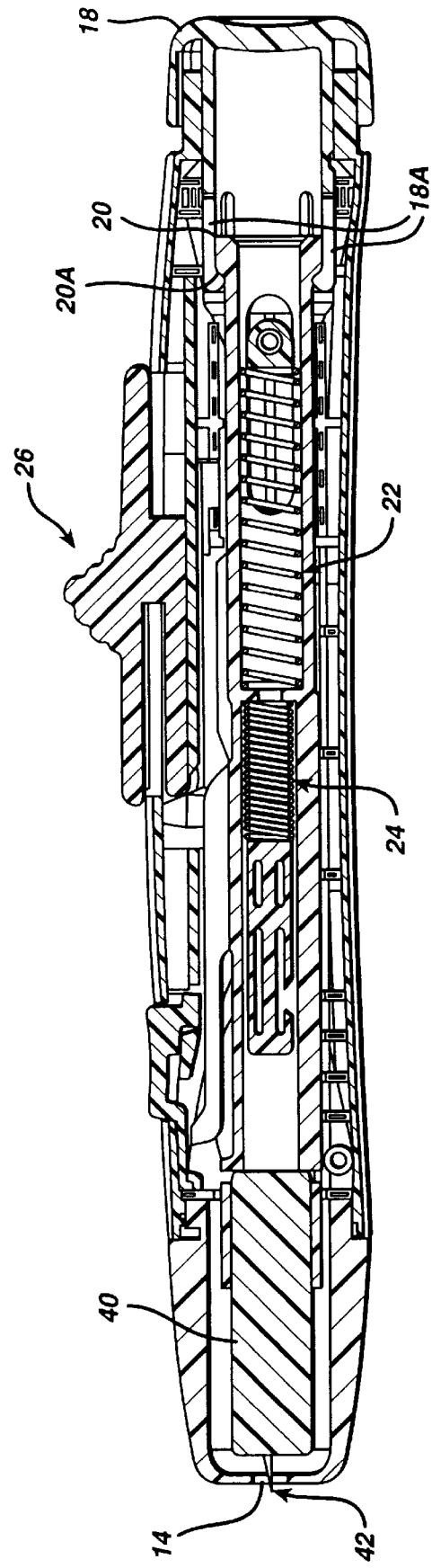
FIG. 6 is a cross section of the device of FIG. 1 as it is being fired.

That sequence leads to the instantaneous situation depicted in FIG. 6, in which lancet 40 has reached its extreme left position, with needle 42 protruding through cap opening 14. Lancet holder 20 has been stopped in its forward (leftward) motion by protuberances on cantilever fingers 18A, which are internal elements of knob 18. As was discussed earlier, the cantilever fingers deflect slightly, whereby they absorb some vibration and reduce noise to reduce pain to the user. These effects are enhanced, in the preferred embodiment shown, by the protuberances on fingers 18A and ledge 20A being cut at a matching angle, so that they make contact over a large area. Slider 26 is still at its initial position. Drive spring 22 has been thrown forward with holder 20 and is uncompressed. Retraction spring 24 is compressed, whereby it will exert a force rearward (to the right) on holder 20, with the result that lancet 40 and needle 42 will be retracted and the configuration of the elements will return to that shown in FIG. 2.

It will be understood by those skilled in the art that the foregoing description and figures are illustrative of practicing the present invention, but are in no way limiting. Variations of the detail presented herein may be made without departing from the scope and spirit of the present invention.

We claim:

1. A lancing device for withdrawing a blood sample, comprising a generally elongate housing having a forward end and a back end, a cap with a through hole at the forward end and containing
   (a) a lancet holder, slidably mounted within the housing,
   (b) a first spring for urging the holder forward, having a first end that bears on the housing and a second end that bears on the holder,
   (c) a slider, slidably mounted in a wall of the housing, comprising
      (i) a projection outside the wall and
      (ii) a pushing means, reversibly engageable with the holder, to push the holder back into a cocked position and to push a lancet forward from the device,
   (d) a second spring for urging the holder back, having a first end that bears on the holder and a second end that bears on the slider,
   (e) a button, movable between a first position in which the holder is restrained when the device is cocked and a second position in which the restraint is removed, permitting the first spring to thrust the holder forward, and
   (f) a closure at the back end, comprising
      (i) a plurality of forward-extending elements for stopping the forward motion of the holder at a predetermined position and
      (ii) adjustment means for controllably changing and resetting the predetermined position.

2. The device of claim 1 in which the forward-extending elements comprise cantilever fingers having inward-extending protrusions for engaging a surface of the holder.

3. The device of claim 1 in which the adjustment means comprises a helical thread for attaching the closure to the housing, whereby rotating the closure on the housing positions the forward-extending elements forward and back.

* * * * *